United States Patent [19]
Reiss et al.

[11] 4,067,914
[45] Jan. 10, 1978

[54] MANUFACTURE OF BUTYNEDIOL

[75] Inventors: Wolfgang Reiss, Ludwigshafen; Siegfried Winderl, Heidelberg-Wieblingen; Wolfgang Schroeder, Bad Durkheim; Herwig Hoffmann, Frankenthal, all of Germany

[73] Assignee: BASF Aktiengesellschaft, Ludwigshafen, Germany

[21] Appl. No.: 671,384

[22] Filed: Mar. 29, 1976

[30] Foreign Application Priority Data

Apr. 5, 1975  Germany .............................. 2514990

[51] Int. Cl.² ............................................. C07C 29/00
[52] U.S. Cl. .................................................. 260/635 Y
[58] Field of Search ...................................... 260/635 Y

[56] References Cited

U.S. PATENT DOCUMENTS

| 3,560,576 | 2/1971 | Kirchner | 260/635 Y |
| 3,723,545 | 3/1973 | Nagel et al. | 260/635 Y |
| 3,920,759 | 11/1975 | Hort | 260/635 Y |

FOREIGN PATENT DOCUMENTS

2,206,693  8/1973  Germany ............................ 260/635Y

*Primary Examiner*—Joseph E. Evans
*Attorney, Agent, or Firm*—Keil, Thompson & Shurtleff

[57] ABSTRACT

In a process for the manufacture of butynediol by the reaction of formaldehyde and acetylene in aqueous solution, in which a catalyst is used which is produced by the action of acetylene and formaldehyde on copper (II) compounds, the catalyst becomes inactive when it is treated for a relatively long period with formaldehyde at elevated temperature in the absence of acetylene so that it must constantly remain in contact with acetylene-containing solution if its temperature is above 70° C.

3 Claims, 2 Drawing Figures

MANUFACTURE OF BUTYNEDIOL

This invention relates to a process for the continuous manufacture of butynediol by reaction of acetylene with formaldehyde in aqueous solution at a temperature between about 60° and 100° C and in contact with a copper acetylide-containing catalyst suspended in the reaction mixture.

Unlike the processes involving fixed bed catalysts, the prior art processes, described in a number of places, involve separation of the reaction mixture showing a depletion of acetylene and formaldehyde from the catalyst by mechanical means, for example filtration, and isolation of butynediol from the catalyst-free reaction mixture containing essentially water and butynediol.

In processes involving the use of suspended catalysts, an increase in the surface of the catalyst should give an increase in the reaction rate. Thus it should be possible to dispense with the use of elevated acetylene pressure. As is well known, plants in which acetylene is used at elevated pressure need to withstand 12 times the maximum reaction pressure expected, for safety reasons.

However, processes using suspended catalysts have not hitherto been generally adopted for a variety of reasons. German Published Application No. 2,206,693 proposes, for example, that the active components be applied to a particulate support in order to obtain an adequate reaction rate. A relatively high concentration of catalyst is used, this giving the reaction mixture a relatively pasty consistency. Thick catalyst suspensions make it difficult to achieve uniform gas distribution in the reactor and are difficult to convey by pumping. For these reasons, U.S. Pat. No. 3,560,576 proposes the use of a non-supported copper compound, e.g. malachite, as catalyst precursor, which is converted to a catalytically active copper acetylide/formaldehyde complex during the reaction of acetylene and formaldehyde at high yield by weight. However, no publication, as yet, has disclosed that this process has been carried out on an industrial scale, the reason for this perhaps being that such a catalyst readily assumes an explosive state. It has also been found that the separation of such catalysts, for example by built-in filters, is difficult to carry out industrially.

Our copending applications Ser. Nos. 525,317 and 613,525 now U.S. Pat. Nos. 3,954,669 and 4,009,124, respectively, describe catalysts having layer lattice crystal structure containing copper, magnesium and aluminum or copper and aluminum in the form of basic carbonates, which catalysts would seem to be a promising approach to an industrial suspension process for the manufacture of butynediol.

Tests on the possibilities of carrying out such a process have shown that the separation of the catalysts from the liquid reaction mixture to be worked up presents certain difficulties manifested by reduction or loss of catalyst activity in the course of time.

Thus it is an object of the invention to provide measures for avoiding the loss of activity of suspension catalysts over a period of time.

We have now found that a process for the continuous manufacture of butynediol by reaction of acetylene with formaldehyde in aqueous solution at a temperature of from about 60° to 100° C in contact with a copper acetylide-containing catalyst suspended in the reaction mixture may be improved if the reaction mixture is withdrawn from the reaction zone together with the suspended catalyst and the catalyst is separated from the reaction mixture in such a manner that it does not remain in contact with substantially acetylene-free formaldehydecontaining solution for more than 5 minutes at temperatures above 60° C.

This invention results from the observation that highly active particulate copper compounds suitable for use as suspension catalysts show a reduction in activity when they remain in contact with solutions containing appreciable amounts of formaldehyde at elevated temperature in the absence of acetylene. A formaldehyde content of at least 5% by weight and an acetylene content of less than 1% by weight are capable of causing such loss of activity at temperatures above about 60° C, time, of course, being the important factor. This is particularly applicable to catalysts obtained from basic copper/aluminum carbonates of the approximate composition $Cu_mAl_n(CO_3)_{0.5m}(OH)_{m+3}$, where m/n may have a value ranging from 2/3 to 1 ("catalyst precursor") or their dehydration products obtained by tempering, by reaction with acetylene.

These catalyst precursors and their manufacture are described in the copending application Ser. No. 613,525 incorporated herein by reference.

The reaction mixture in which the catalyst is suspended contains the same generally in an amount of from about 2 to 25% and particularly advantageously from 5 to 20%, by weight.

According to the invention, when the reaction mixture containing suspended catalysts leaves the reactor, it is cooled to a temperature below 60° C and preferably below 40° C in a period of less than 5 minutes and preferably less than 2 minutes, as measured from the moment of leaving the reactor, or the catalyst is separated therefrom during this period and recycled to the reaction zone. It will be appreciated that simultaneous separation and cooling and recycling in as short a time as possible is particularly advantageous. It is necessary, of course, to avoid a corresponding reduction in the acetylene concentration of the reaction mixture within the reactor whilst the formaldehyde concentration remains appreciable. This is generally ensured in the case of reactors of the stirred vessel type, i.e. reaction chambers showing more or less ideal backmixing behavior. Where a tubular reactor is used, as is industrially possible and is in some cases not without advantage, the invention naturally demands that that portion of the reaction zone which is not subjected to cooling should contain an adequate residual concentration of acetylene in the steady state. For purely economical reasons, i.e. to avoid the use of unduly large reactors or unduly long reaction zones, the arrangement will, of course, be such as to ensure that the reaction takes place over as much of the reaction chamber as possible.

Suitable residual concentrations of acetylene necessary to avoid impairment of the catalyst at the reaction temperature over a short residence time may generally be taken to be from $0.5 \times 10^{-2}$ to $2 \times 10^{-2}$ percent, by weight, calculated as units of weight of acetylene per unit of weight of reaction mixture calculated as free from catalyst. Chemically speaking, the pressure at which the process is carried out is not critical and may be, say, from 1 to 30 bars. For practical reasons, however, it is preferred to use pressures near atmospheric, e.g. from 1 to 5 bars, as indicated above.

According to the invention, the thus acetylene-depleted suspension leaving the reactor is, for example, passed as quickly as possible through a cooler, where it is cooled to a temperature generally below 40° C. The reaction product is then separated from the catalyst in the usual manner.

It is particularly advantageous to use a settling vessel for this purpose, from the base of which a concentrated suspension is withdrawn and returned to the reactor. The concentration of catalyst in this concentrated suspension is generally between 15 and 35% by weight. Suspensions in which the catalyst concentration is greater may cause conveying difficulties.

Under these conditions, it is possible to remove a clear suspension from the top portion of the settling vessel, the content of suspended matter in said suspension being less than 20 ppm. The necessary and admissible residence time in the settling vessel (at a temperature below 40° C) is from 1 to 3 hours. It is frequently convenient to clarify the resulting clear solution by means of a fine filter.

It has been found that small amounts of formic acid are formed during the reaction. Since the reaction giving butynediol should be carried out in virtually neutral medium (pH's from 6.5 to 7.2), it is recommended to add controlled amounts of a neutralizing agent, preferably aqueous caustic soda, as is usual in the prior art.

The invention will be further appreciated with the aid of the drawing, wherein.

EXAMPLE

The reactor substantially consists of a vertical cylinder of 18/8 steel. Near the bottom of the reactor there is provided a perforated plate. The diameter of each perforation is 1 mm and the free cross-section is 1.5%. The starting materials formaldehyde (in 30% aqueous solution) and acetylene are fed to the chamber below the plate and pass through the perforated plate to the reaction chamber. The reaction temperature is 80° C and is maintained sufficiently constant by the usual industrial methods. The pressure in the reactor is about 1 bar.

The concentration in the reactor of the copper-aluminum compound used as a catalyst precursor is 8% by weight. The catalyst specially prepared for this purpose has the composition $Cu_5Al_6(CO_3)_{2.5}(OH)_{17}O_3$ and is one of a group of compounds of the general formula $Cu_mAl_6(CO_3)_{0.5m}(OH)_{m+18}$ or a water-depleted modification thereof. Such compounds may be obtained by preparing an approximately 1M aqueous solution of precipitable salts of copper and aluminum containing copper and aluminum in an atomic ratio of copper:aluminum of m:6 and mixing the solution with a solution containing alkali metal carbonate and/or bicarbonate, this being an approximately 2n solution of alkali metal ions, mixing being carried out so as to give a pH of from 8 to 9.5 and preferably from 8.1 to 8.5 in the mixture, whilst a mixing temperature of from 60° to 90° C is maintained, whereupon the resulting precipitate is washed if necessary and then dried at a temperature below 100° C.

By determining the carbon dioxide, the titrable water according to Fischer and the total loss on ignition and by determining the content of copper and aluminum in appropriate samples in the usual manner, it was possible to arrive at the above probable formula.

Figure 1:
FIG. 1 is an X-ray diagram of the compounds produced in the example below.
Figure 2:
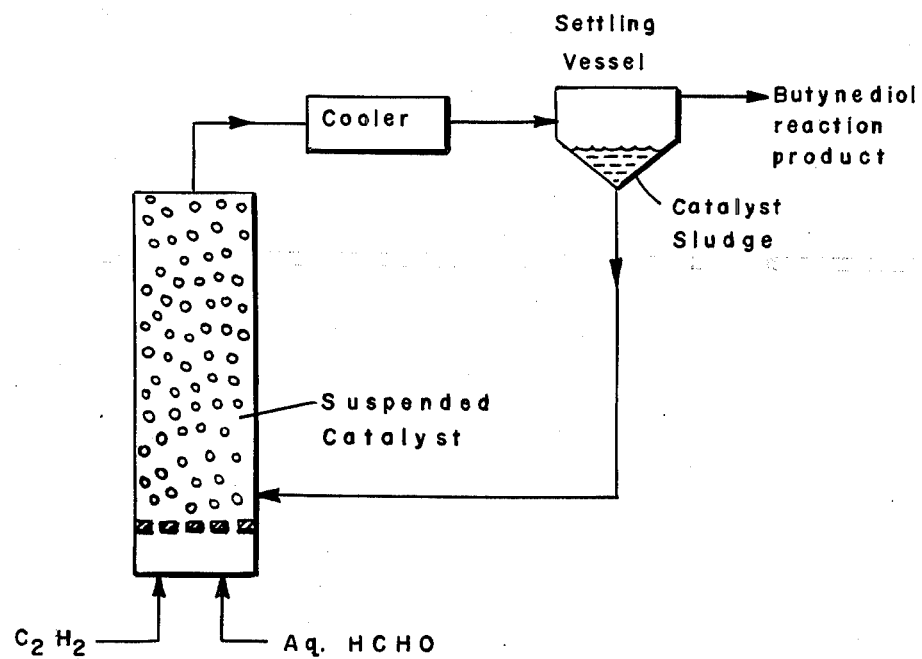
FIG. 2 is a diagrammatic illustration of the process.

The X-ray diagrams of the compounds (see Table below and FIG. 1, the compound having the composition $Cu_5Al_6(CO_3)_{2.5}(OH)_{17}O_3$) indicate a layer lattice.

TABLE d values of Guinier photographs (CuKα)
$Cu_5Al_6$ carbonate
1)

| d | relative intensity |
|---|---|
| 7.65 | 100 |
| 3.80 | 90 |
| 2.72 | 50 |
| 2.52 | 70 |
| 2.41 | 40 |
| 2.39 | 10 |
| 2.24 | 50 |
| 2.03 | 20 |
| 1.89 | 50 |
| 1.72 | 30 |
| 1.59 | 10 |
| 1.56 | 30 |
| 1.54 | 10 |
| 1.52 | 30 |
| 1.47 | 30 |
| 1.44 | 30 |

REMARKS

The $d$ values may deviate slightly from the above values depending on the water content of the samples. Small amounts of impurities ($Al(OH)_3$) are usually found.

Lines of low relative intensity were not measured, i.e. the list contains only the main lines.

This catalyst precursor may be obtained by precipitation from aqueous salt solution with a basic, carbonate-containing precipitant in aqueous solution. It is important to maintain relatively narrow pH and temperature ranges. It has been found to be particularly advantageous to carry out precipitation under alkaline conditons, particularly in a pH range of from 8.0 to 8.5, and to use a temperature of from 60° to 90° C and in particular from 75° to 85° C. Examples of suitable salts are nitrates, sulfates, acetates, formates and other water-soluble salts.

Suitable precipitants are alkali metal carbonates and bicarbonates, particularly sodium bicarbonate or mixtures of sodium carbonate and sodium bicarbonate, possible in admixture with sodium hydroxide if the salts used give a relatively strong acid reaction. A particularly suitable precipitant is a solution obtained by heating water with (sparingly soluble) sodium bicarbonate in an amount of from 100 to 200 g/l, heating being continued until the bicarbonate is completely dissolved. This causes liberation of carbon dioxide and conversion of a portion of the bicarbonate to carbonate, in known manner. The metal salt is conveniently used in 1M to 2M solution and the precipitant in 1n to 2n solution. Precipitation may be effected continuously or batchwise.

The precipitate is washed free from nitrate and is preferably dehydrated by spray drying to form spherical particles having diameters of from 20 to 150μm. The catalyst precursor is then formed from this compound generally by tempering for from 1 to 8 hours and in particular for from 1 to 2 hours at temperatures of from 500 to 600° C.

The relationship of reactor capacity and feed rate gives a residence time of 5 hours. The linear gas velocity through the perforated plate is 3 cm/s (calculated for an empty reactor).

The pH of the reaction medium is maintained between 7 and 7.2 by controlled addition of aqueous caustic soda. The reaction product is withdrawn at the top of the reactor and immediately passes to the cooler. The temperature of the product on leaving the cooler is about 35° C. Entrained gas bubbles can escape in the degasifier.

The cold suspension then passes to the settling vessel. The residence time is 1.5 hours. The readily pumpable catalyst sludge containing 20% by weight of catalyst is withdrawn from the bottom of the settler and recycled to the reactor. The clarified reaction product is removed at the top of the settler. Under steady state conditions, the clarified product contains less than 20 ppm of suspended matter. Separation of this suspended matter is effected by pumping the product through a filter which can be back-rinsed, whereupon it passes to the tank. A portion of this solution is used, when necessary, for back-rinsing the filter. The back-rinsed suspended matter passes to a separate tank, from which it may be recycled to the reactor or removed from the process. The catalyst is found to have retained its original activity and settling properties after an onstream period of 50 days. 1 kg of the catalyst in the reactor produces 15 kg of butynediol, per day, the total byproducts contained in the reaction solution being less than 1%.

COMPARATIVE TEST

The Example is repeated except that the flow of cooling water to the cooler is stopped. The temperature in the settling vessel rises to above 70° C. Within one day, the butynediol concentration in the reaction product drops to a few percent by weight and the formation of high-boiling dark-colored byproducts increases rapidly until their concentration is from 3 to 5%. When the cooler is re-started it is found that no reactivation of the catalyst takes place, this having been damaged irreversibly.

We claim:

1. In a process for the continuous manufacture of butynediol by reaction of acetylene with formaldehyde in aqueous solution at a temperature of from about 60° to 100° C in a reaction chamber in contact with a copper acetylide-containing catalyst suspended in the reaction mixture, withdrawing a portion of the reaction mixture, said withdrawn portion being essentially free from acetylene and comprising an aqueous solution of aqueous formaldehyde, butynediol and suspended copper acetylide-containing catalyst, and separating said suspended catalyst from said withdrawn portion, the improvement comprising separating said copper acetylide-containing catalyst which is suspended in said withdrawn portion under conditions wherein said catalyst remains in contact with the substantially acetylene-free withdrawn portion of said reaction mixture for a period of not more than five minutes at temperatures above 60° C.

2. A process as claimed in claim 1, wherein cooling to a temperature below 40° C is complete not later than 5 minutes after the moment at which the concentration of acetylene in the reaction mixture falls below $0.5 \times 10^{-2}$ percent by weight of acetylene, based on the catalyst-free reaction mixture.

3. A process as claimed in claim 1, wherein the catalyst used is a reaction product of a compound of the approximate empirical formula $Cu_m Al_n(CO_3)_{0.5m}(OH)_{m+3n}$, wherein m/n may have a value of from 2/3 to 1, or its dehydration products, with acetylene in the form of a suspension, said reaction product forming essentially spherical particles having diameters of from 5 to 250 μm.

* * * * *